US012649052B2

(12) United States Patent
Jung et al.

(10) Patent No.: US 12,649,052 B2
(45) Date of Patent: Jun. 9, 2026

(54) MULTI-LAYER MICRONEEDLE STRUCTURE AND METHOD FOR MANUFACTURING SAME

(71) Applicant: INDUSTRY-ACADEMIC COOPERATION FOUNDATION, YONSEI UNIVERSITY, Seoul (KR)

(72) Inventors: Hyung Il Jung, Seoul (KR); Jeong Yun You, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 716 days.

(21) Appl. No.: 18/003,870

(22) PCT Filed: Jul. 5, 2021

(86) PCT No.: PCT/IB2021/056002
§ 371 (c)(1),
(2) Date: Dec. 29, 2022

(87) PCT Pub. No.: WO2022/003653
PCT Pub. Date: Jan. 6, 2022

(65) Prior Publication Data
US 2023/0256218 A1 Aug. 17, 2023

(30) Foreign Application Priority Data
Jul. 2, 2020 (KR) ........................ 10-2020-0081467

(51) Int. Cl.
*A61M 37/00* (2006.01)
(52) U.S. Cl.
CPC . *A61M 37/0015* (2013.01); *A61M 2037/0023* (2013.01); *A61M 2037/0053* (2013.01)

(58) Field of Classification Search
CPC .. A61M 2037/0023; A61M 2037/0046; A61M 2037/003; A61M 37/0015; A61M 2037/0053
See application file for complete search history.

(56) References Cited

U.S. PATENT DOCUMENTS

2011/0240201 A1* 10/2011 Jung ................... B32B 37/1292
156/60
2016/0067469 A1 3/2016 Jung et al.
(Continued)

FOREIGN PATENT DOCUMENTS

CN 109364017 A 2/2019
JP 2012-217653 A 11/2012
(Continued)

OTHER PUBLICATIONS

Office Action in Japanese Patent Application No. 2022-581643 issued on Dec. 12, 2023.
(Continued)

*Primary Examiner* — Deanna K Hall
(74) *Attorney, Agent, or Firm* — Knobbe, Martens, Olson & Bear, LLP

(57) ABSTRACT

A multi-layer microneedle structure and a method for manufacturing same are provided. The multi-layer microneedle structure includes: a base layer formed on a support; a core layer formed on the base layer and containing a drug; and a shell layer formed on the base layer to cover the core layer. Herein, the relationship between the thickness T of the shell layer outside the core layer and the height H2 of the core layer is determined according to the material constituting the core layer.

19 Claims, 13 Drawing Sheets

<u>10</u>

(56) References Cited

U.S. PATENT DOCUMENTS

| | | |
|---|---|---|
| 2017/0354610 A1 | 12/2017 | Jung et al. |
| 2018/0200157 A1 | 7/2018 | Jung et al. |
| 2019/0183405 A1 | 6/2019 | Lee et al. |

FOREIGN PATENT DOCUMENTS

| | | |
|---|---|---|
| JP | 2018-502684 A | 2/2018 |
| JP | 2020-512283 A | 4/2020 |
| KR | 10-2012-0068516 A | 6/2012 |
| KR | 10-2016-0073337 A | 6/2016 |
| KR | 10-2017-0008183 A | 1/2017 |
| KR | 10-2017-0044049 A | 4/2017 |
| KR | 10-2019-0123642 A | 11/2019 |
| KR | 10-2020-0024515 A | 3/2020 |
| KR | 10-2020-0085224 A | 7/2020 |
| WO | 2014/197995 A1 | 12/2014 |
| WO | WO 2017/090254 A1 | 6/2017 |
| WO | WO 2017/104144 A1 | 6/2017 |

OTHER PUBLICATIONS

Kim et al., "Droplet-born air blowing: Novel dissolving microneedle fabrication", Journal of Controlled Release, vol. 170, No. 3, Jun. 3, 2013, pp. 430-436.

Yang et al., "Centrifugal Lithography: Self-Shaping of Polymer Microstructures Encapsulating Biopharmaceutics by Centrifuging Polymer Drops", Advanced Healthcare Materials, vol. 6, No. 19, Jul. 13, 2017, 7 pages.

Office Action issued in Korean Patent Application No. 10-2020-0081467, dated Mar. 19, 2024 in 10 pages.

Office Action including Extended European Search Report issued in European Patent Application No. 21832535.5, dated Jul. 2, 2024 in 17 pages.

International Search Report in PCT Application No. PCT/IB2021/056002 dated Nov. 2, 2021.

Office Action received in corresponding IN Patent Application No. 202317000162 dated Oct. 6, 2025.

\* cited by examiner (a)

(b)

(a)                    (b)

(a)                    (b)                    (c)

(a)          (b)          (c)

MULTI-LAYER MICRONEEDLE STRUCTURE AND METHOD FOR MANUFACTURING SAME

TECHNICAL FIELD

The present invention relates to a multi-layer microneedle structure and a method for manufacturing the same.

BACKGROUND ART

A dissolving microneedle (DMN) is a promising alternative approach to subcutaneous injection and oral administration which are most widely used as a drug delivery system in the medical field. The microneedle improves a delivery speed of therapeutic agents through a mechanism that directly induces the drug to an epidermal or dermal region, while also improving patient convenience due to less pain than subcutaneous injection.

However, loss of drugs, particularly biopharmaceuticals or oxygen-sensitive drugs, during the manufacturing and storage process of the microneedle structure causes a significant obstacle in replacing the conventional drug delivery systems with the microneedle structure.

In addition, although many attempts have been made to achieve the delivery and maintenance of a fixed amount of drugs, the technology for preserving drugs and the technology for delivering a fixed amount of drugs solve only one problem for each. Therefore, a new strategy capable of simultaneously satisfying them is required.

(Patent Document 1) KR 2019-0123642 A

DISCLOSURE

Technical Tasks

In order to solve the problems of the prior art as described above, an embodiment of the present invention is to provide a multi-layer microneedle structure capable of preventing loss of a drug during a manufacturing process while delivering a fixed amount of drug, and a manufacturing method thereof.

However, the problems to be solved by the present invention are not limited to the above-mentioned problems, and other problems not mentioned will be clearly understood by those skilled in the art from the following description.

Technical Solution

According to one aspect of the present invention for solving the above problems, there is provided a multi-layer microneedle structure including: a base layer formed on a support; a core layer formed on the base layer and containing a drug; and a shell layer formed on the base layer to cover the core layer, wherein the relationship between the thickness T of the shell layer outside the core layer and the height H2 of the core layer is determined according to the material constituting the core layer.

In an embodiment, the core layer may be made of a hydrophilic material, and the height H2 of the core layer may be inversely proportional to the thickness T of the shell layer outside the core layer.

In an embodiment, the core layer may be made of a hydrophobic material, and the height H2 of the core layer may be constant regardless of the thickness T of the shell layer outside the core layer.

In an embodiment, the thickness T of the shell layer outside the core layer may be inversely proportional to the fluidization process time for forming the core layer and the shell layer.

In an embodiment, the thickness T of the shell layer outside the core layer may be the smallest at a bonding surface between the core layer and the base layer.

In an embodiment, the thickness T of the shell layer outside the core layer may be uniform throughout the core layer.

In an embodiment, when the total height H of the base layer, the core layer and the shell layer, and the height H1 of the base layer are constant, the height H2 of the core layer may be inversely proportional to the height H3 from the tip of the core layer to the tip of the shell layer.

In an embodiment, the base layer may have a micro-cavity on an upper side thereof, and the core layer may be made of powder or liquid and may be provided in the micro-cavity.

In an embodiment, the height H2 of the core layer may be determined by the height of the micro-cavity.

In an embodiment, the base layer may be formed on micro-pillars formed on the support.

In an embodiment, the support may be a perforated plate having an opening, and the base layer may be formed by filling the opening.

According to another aspect of the present invention, there is provided a method of manufacturing a multi-layer microneedle structure, the method including: a first dispensing step of dispensing a first composition on a support; a drying step of drying the first composition to form a base layer; a second dispensing step of dispensing a second composition comprising a drug on the base layer; a third dispensing step of dispensing a third composition on the base layer to cover the second composition; and a forming step of forming a core layer from the second composition and a shell layer from the third composition.

In an embodiment, the forming step may be performed by fluidization, centrifugal lithography technique, or droplet born air blowing (DAB).

In an embodiment, the second composition may be made of a hydrophilic material, and the height H2 of the core layer may be proportional to the fluidization process time.

In an embodiment, the second composition may be made of a hydrophobic material, and the height H2 of the core layer may be constant regardless of the fluidization process time.

In an embodiment, the thickness T of the shell layer outside the core layer and the height H3 from the tip of the core layer to the tip of the shell layer may be inversely proportional to the fluidization process time.

In an embodiment, the drying step may further comprise forming a micro-cavity on the base layer, and the second composition may be made of powder or liquid, wherein in the second dispensing step, the second composition may be dispensed in the micro-cavity.

In an embodiment, the support may include micro-pillars, wherein in the first dispensing step, the first composition may be dispensed on the micro-pillars.

In an embodiment, the support may be a perforated plate having an opening, wherein in the first dispensing step, the first composition may be filled in the opening.

In an embodiment, the second dispensing step may further include drying the second composition.

Advantageous Effects

In the multi-layer microneedle structure and manufacturing method thereof according to an embodiment of the present invention, the shell layer is provided as a multi-layer structure to cover the core layer containing a drug, so that exposure and release of the drug can be blocked by the shell layer, thereby preventing loss of the drug in the manufacturing process.

In addition, according to the present invention, since the core layer is formed on the base layer that does not contain the drug, the core layer containing the drug can be sufficiently inserted into the skin, and thus, the drug can be delivered in a fixed quantity.

In addition, according to the present invention, since the multi-layer microneedle structure can be formed by the shell layer disposed at the outermost portion, a microneedle structure for various drugs can be manufactured by the same process under the same manufacturing conditions regardless of the type of drug included in the core layer.

Further, according to the present invention, since the core layer is formed so as not to be exposed to the outside, there is no need to optimize the manufacturing process according to the type of drug, thereby simplifying the manufacturing process and improving manufacturing efficiency.

In addition, according to the present invention, by changing the manufacturing conditions for the shell layer, the physical properties of the entire multi-layer microneedle structure can be improved, and the drug can be safely protected from the external environment.

EMBODIMENTS

Figure 1:
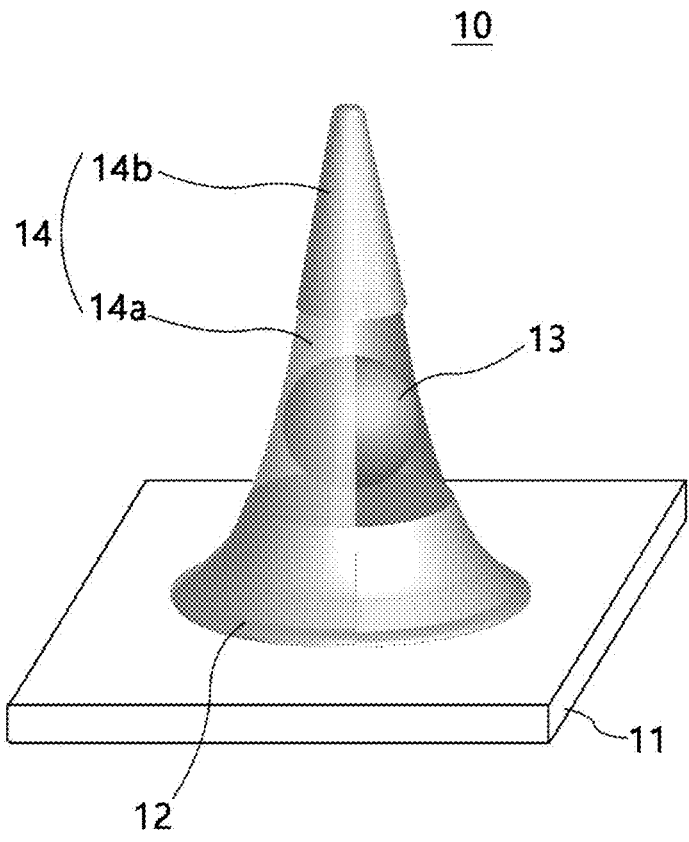
FIG. 1 is a perspective view showing a multi-layer microneedle structure according to an embodiment of the present invention.

Hereinafter, with reference to the accompanying drawings, embodiments of the present invention will be described in detail so as to be easily implemented by one of ordinary skill in the art to which the present invention pertains. The present invention may be embodied in a variety of forms and is not limited to the embodiments described herein. In order to clearly describe the present invention in the drawing, parts irrelevant to the description are omitted from the drawings; and throughout the specification, same or similar components are referred to as like reference numerals.

Embodiments of the present invention are provided to more completely describe the present invention to those skilled in the art. The embodiments described below may be modified in various different forms, and the scope of the present invention is not limited to the following embodiments. Rather, these embodiments are provided so as to make the present invention more faithful and complete, and to fully convey the spirit of the present invention to those skilled in the art.

Hereinafter, embodiments of the present invention will be described with reference to the drawings schematically illustrating embodiments of the present invention. In the drawings, variations in the illustrated shape may be expected, for example depending on manufacturing technology and/or tolerance. Therefore, the embodiments of the present invention should not be construed as limited to the specific shape shown in the drawings, but should include, for example, a change in shape caused during manufacturing.

Figure 2:
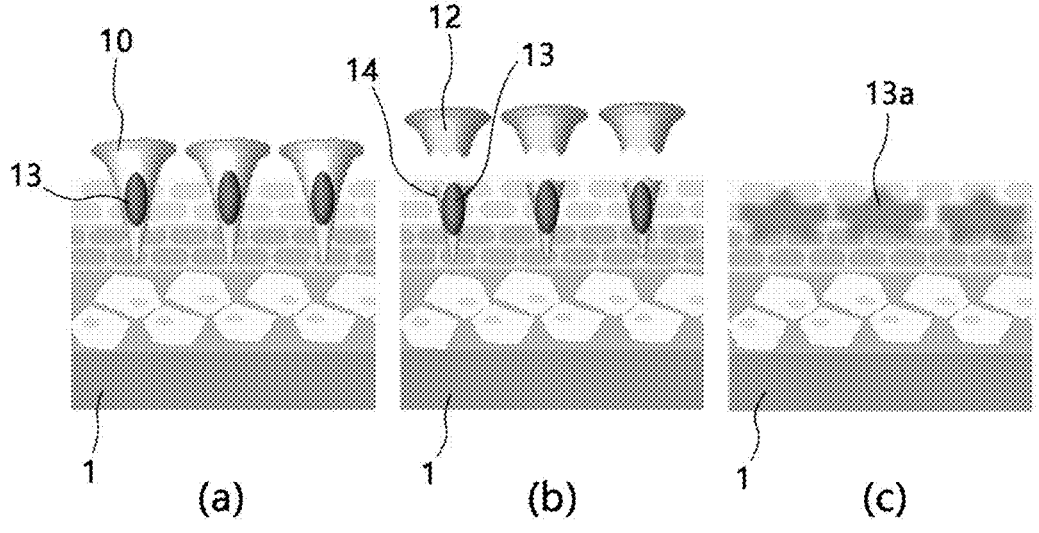
FIG. 2 is a view showing an application example of a multi-layer microneedle structure according to an embodiment of the present invention.
Figure 3:
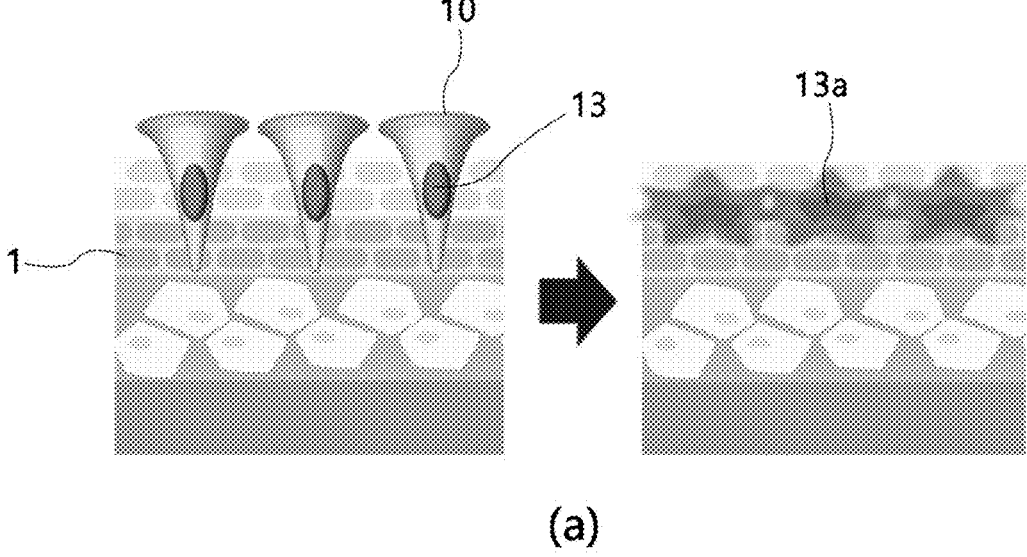
FIG. 3 is a view showing an in vitro experiment and results of a multi-layer microneedle structure according to an embodiment of the present invention.
Figure 3:
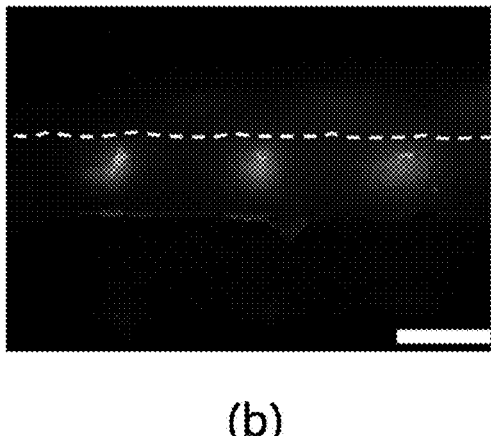

FIG. 1 is a perspective view showing a multi-layer microneedle structure according to an embodiment of the present invention; FIG. 2 is a view showing an application example of a multi-layer microneedle structure according to an embodiment of the present invention; and FIG. 3 is a view showing an in vitro experiment and results of a multi-layer microneedle structure according to an embodiment of the present invention.

Referring to FIG. 1, a multi-layer microneedle structure 10 according to an embodiment of the present invention includes a base layer 12, a core layer 13, and a shell layer 14.

The base layer 12 is formed to a certain height on a support 11. The base layer 12 is to help deliver a fixed amount of drug, and as shown in FIG. 2, may be formed to a certain height so that the core layer 13 containing the drug can be sufficiently inserted into a skin. Therefore, the base layer 12 does not contain any drug.

Therefore, the multi-layer microneedle structure 10 according to an embodiment of the present invention can reliably ensure the delivery of a fixed amount of drug because the core layer 13 containing the drug can be sufficiently inserted into the skin 1.

The core layer 13 is a site for loading an effective drug, and is formed on the base layer 12. Here, the core layer 13 may be made of a hydrophilic material or a hydrophobic material. For example, the core layer 13 may include hyaluronic acid (HA) or polycaprolactone (PCL), but is not limited thereto. In addition, the core layer 13 may be formed of powder or liquid.

In this case, the core layer 13 may have various shapes depending on the material to be used. For example, when the core layer 13 is made of a hydrophilic material, it may have a shape similar to that of the shell layer 14 (see FIG. 6). That is, since the core layer 13 is affected by the fluidization process, it may be formed in s similar shape to that of a tip portion 14b of the shell layer 14.

Alternatively, when the core layer 13 is made of a hydrophobic material, as shown in FIG. 1, it may be provided in a circular shape in the shell layer 14. Here, the shape of the core layer 13 is not particularly limited. The core layer 13 has a shape independent of that of the shell layer 14. That is, unlike the case of the hydrophilic material, the core layer (13) is hardly affected by the fluidization process, and thus, is not formed in a shape similar to that of the tip portion 14b of the shell layer 14.

The shell layer 14 is to form the overall shape of the multi-layer microneedle structure 10 and is formed on the base layer 12 to cover the core layer 13. Here, the shell layer 14 may be made of a polymer which is not loaded with a drug. As shown in FIG. 1, the shell layer 14 may include a cover layer 14a and a tip portion 14b.

The cover layer 14a is for protecting the drug of the core layer 13 and may completely cover the core layer 13 so as not to be exposed to the outside.

The tip portion 14b may be formed to have a sharp tip so as to be easily inserted into a skin 1. In this case, the shell layer 14 may be made of a material having high physical strength or may be manufactured by a manufacturing process therefor.

As such, the multi-layer microneedle structure 10 may include only the base layer 12 and the shell layer 14 in appearance because the core layer 13 is not exposed to the outside.

Therefore, in the multi-layer microneedle structure 10 according to an embodiment of the present invention, exposure and release of drugs contained in the core layer 13 can be blocked by the shell layer 14, so loss of the drug during the manufacturing and storage can be prevented.

Here, the shell layer 14 may be formed by a centrifugal lithography method using a fluidization process. Accordingly, the shape of the shell layer 14 may be changed according to the fluidization process time.

In this case, the relationship between the thickness T of the shell layer 14 outside the core layer 13 and the height H2 of the core layer 13 may be determined according to a material constituting the core layer 13. Here, the thickness T of the shell layer 14 outside the core layer 13 may be affected by the fluidization process time. That is, the thickness T of the shell layer 14 outside the core layer 13 may be inversely proportional to the fluidization process time (see FIG. 11).

For example, when the core layer 13 is made of a hydrophilic material, the height H2 of the core layer 13 may be affected by the fluidization process time. More specifically, the height H2 of the core layer 13 may be inversely proportional to the thickness T of the shell layer 14 outside the core layer 13. That is, the height H2 of the core layer 13 may increase as the thickness T of the shell layer 14 outside the core layer 13 decreases.

In this case, the height H3 from the tip of the core layer 13 to the tip of the shell layer 14 may decrease as the thickness T of the shell layer 14 outside the core layer 13 decreases. Accordingly, the height H3 from the tip of the core layer 13 to the tip of the shell layer 14 may be proportional to the thickness T of the shell layer 14 outside the core layer 13.

Here, when the total height H of the base layer 12, the core layer 13 and the shell layer 14, and the height H1 of the base layer 12 are constant, the height H2 of the core layer 13 and the height H3 from the tip of the core layer 13 to the tip of the shell layer 14 may be affected by the fluidization process time. In this case, since the height H2 of the core layer 13 increases in proportion to the fluidization process time, the height H2 of the core layer 13 may be inversely proportional to the height H3 from the tip of the core layer 13 to the tip of the shell layer 14.

As another example, when the core layer 13 is made of a hydrophobic material, the height H2 of the core layer 13 is not affected by the fluidization process time. That is, the height H2 of the core layer 13 may be constant regardless of the thickness T of the shell layer 14 outside the core layer 13.

In this case, the thickness T of the shell layer 14 outside the core layer 13 may be 1 to 50 μm. Here, when the thickness T of the shell layer 14 outside the core layer 13 is less than 1 μm, the shell layer 14 does not provide sufficient strength, so that the core layer 13 may be exposed to the outside or may leak from the cover layer 14a. Therefore, the multi-layer microneedle structure 10 does not guarantee safe protection of the drug.

On the other hand, when the thickness T of the shell layer 14 outside the core layer 13 exceeds 50 μm, the shell layer 14 may be redundant than necessary, thereby wasting material without further enhancing the effect of the shell layer 14.

In addition, the thickness T of the shell layer 14 outside the core layer 13 may be different for each location depending on the physical properties or shape of the core layer 13. For example, the thickness T of the shell layer 14 outside the core layer 13 may be the smallest at the bonding surface between the core layer 13 and the base layer 12 (see FIG. 11). Thereby, the multi-layer microneedle structure 10 can be easily manufactured without optimizing the fluidization process conditions.

Figure 6:
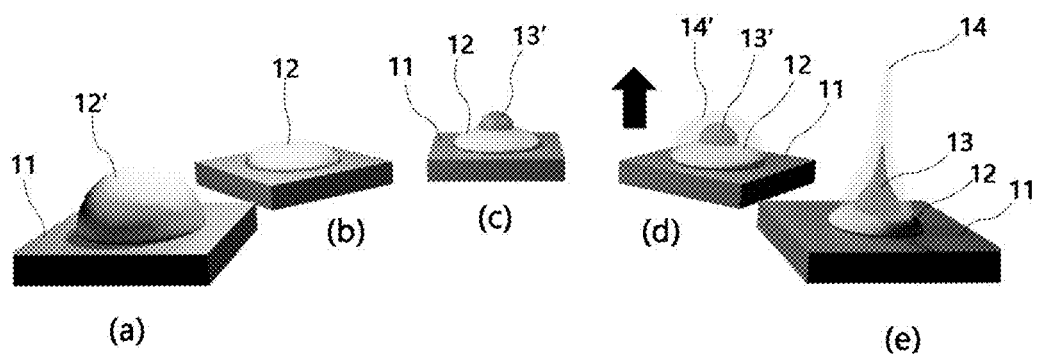
FIG. 6 is a view schematically showing a manufacturing process of a multi-layer microneedle structure according to an embodiment of the present invention.

As another example, the thickness T of the shell layer 14 outside the core layer 13 may be uniform throughout the core layer 13 (see FIG. 6). Therefore, the shell layer 14 can more safely ensure the protection of the drug contained in the core layer (13).

Referring to FIG. 2, when the multi-layer microneedle structure 10 is inserted into the skin 1, the core layer 13 is located in the skin 1 (see FIG. 2(a)). Then, when the base layer 12 is dissolved by the skin 1 or physically or chemically separated from the support 11 (see FIG. 2(b)), the cover layer 14a and the tip portion 14b of the shell layer 14 are dissolved in the skin 1, and the drug 13a is delivered to the skin 1 (see FIG. 2(c)). Thus, the drug 13a contained in the core layer 13 can be delivered to the skin 1 in a predetermined amount without loss.

Referring to FIG. 3, it shows that all the core layers 13 are delivered into the skin 1. After loading different fluorescent materials on each layer of the multi-layer microneedle structure 10, an in vitro insertion test was performed (see FIG. 3(a)). Here, the core layer 13 is loaded with a red fluorescent material, and the shell layer 14 is loaded with a green fluorescent material (see FIG. 3(b)). As shown in the photograph of the skin delivery surface, it can be seen that all the core layers 13 are transferred into the skin 1.

Meanwhile, the multi-layer microneedle structure 10 according to an embodiment of the present invention may be configured in various forms.

For example, the multi-layer microneedle structure 10 may be formed on a support 11 provided with micro-pillars. In this case, the multi-layer microneedle structure 10 may be formed on the micro-pillars.

As another example, the multi-layer microneedle structure 10 may be provided on a perforated plate mounted on an applicator. In this case, the perforated plate is formed to have an opening, and such a perforated plate can be used as a support. That is, the base layer 12 may be formed by filling the opening of the perforated plate. As a result, the multi-layer microneedle structure 10 may be provided on the opening of the perforated plate.

Figure 4:
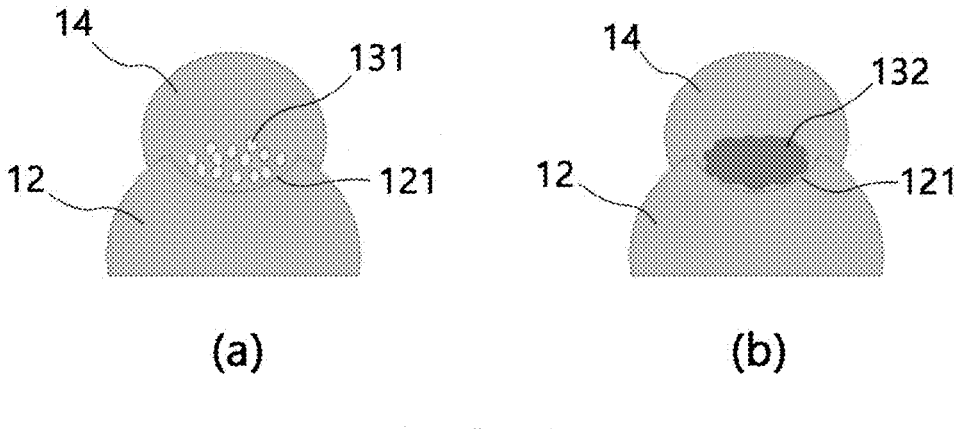
FIG. 4 is a view showing an example of a core layer in a multi-layer microneedle structure according to an embodiment of the present invention.

FIG. 4 is a view showing an example of a core layer in a multi-layer microneedle structure according to an embodiment of the present invention.

Referring to FIG. 4, in the multi-layer microneedle structure 10, the core layer 13 containing the drug may be made of powder or liquid.

In this case, the base layer 12 may have a micro-cavity 121 at an upper side thereof. Here, a powder core layer 131 or a liquid core layer 132 may be provided in the micro-cavity 121. The micro-cavity 121 may be provided in the center of the upper portion of the base layer 12. In addition, the micro-cavity 121 is not particularly limited as long as it has a shape for accommodating the powder core layer 131 or the liquid core layer 132.

Here, the height H2 of the core layer 13 may be determined by the height of the micro-cavity 121. That is, since the powder core layer 131 or the liquid core layer 132 is filled in the micro-cavity 121 and cannot be formed high above the micro-cavity 121 due to its characteristics, the height H2 of the core layer 13 may be substantially equal to, or higher by several μm than, the height of the micro-cavity 121.

Accordingly, since the core layer 13 containing the drug is completely surrounded by the base layer 12 as well as the shell layer 14, the multi-layer microneedle structure 10 can safely protect the drug.

Figure 5:
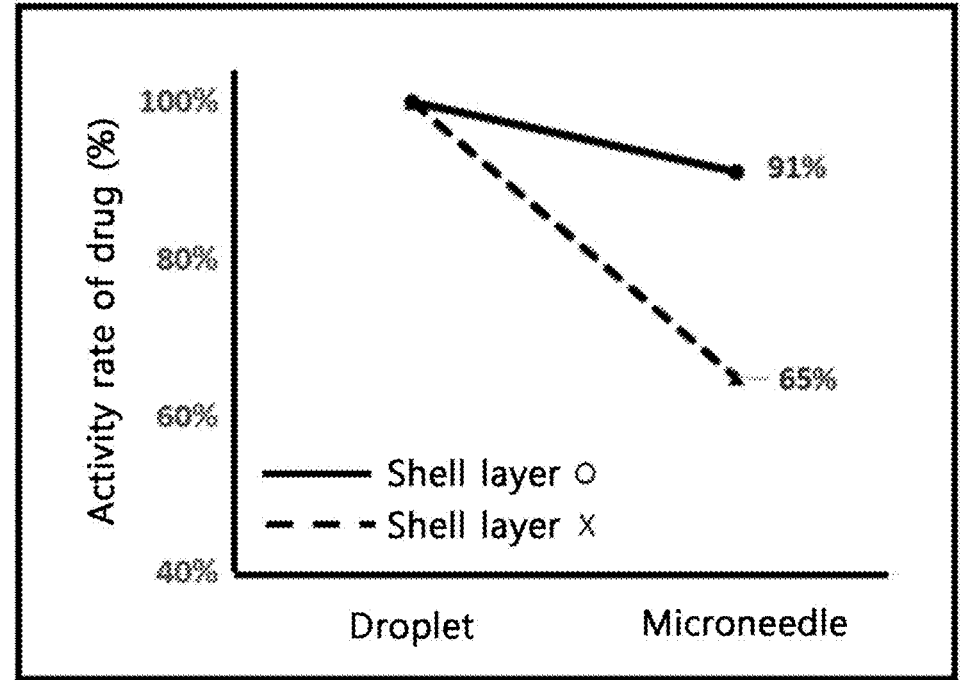
FIG. 5 is a graph showing experimental results verifying the role of a shell layer in a multi-layer microneedle structure according to an embodiment of the present invention.

FIG. 5 is a graph showing experimental results verifying the role of a shell layer in a multi-layer microneedle structure according to an embodiment of the present invention.

The present inventors performed the following experiment to confirm the role of the shell layer 14. First, a multi-layer microneedle structure 10 according to an embodiment of the present invention was prepared. As a comparative example, a microneedle structure having only a core layer 13 containing a drug on a base layer without a shell layer was prepared. In this case, ascorbic acid was used as the drug included in the microneedle structure.

As shown in FIG. 5, in the case of a droplet before forming a microstructure, the activity rate of ascorbic acid is 100% for both cases with and without the shell layer, but in the completely fabricated microneedle structure, the activity rate of ascorbic acid in the case of having the shell layer was 91%, and the activity rate of ascorbic acid in the case of not having the shell layer was 65%. As a result, it can be seen that the loss of the drug is effectively prevented by the shell layer.

FIG. 6 is a view schematically showing a manufacturing process of a multi-layer microneedle structure according to an embodiment of the present invention.

Referring to FIG. 6, in a manufacturing process of the multi-layer microneedle structure according to an embodiment of the present invention, first, a first composition 12' is dispensed to a support 11 ((a) first dispensing step). Here, the support 11 may be made of a biocompatible material. In addition, the first composition 12' is not loaded with a drug.

Next, the first composition 12' is dried to form a base layer 12 ((b) drying step). Here, the base layer 12 is to help deliver a fixed amount of drug, and may be formed to a certain height so that a core layer 13 containing a drug can be sufficiently inserted into a skin.

Optionally, when a second composition 13' is made of powder or liquid, a micro-cavity may be formed on the base layer 12 (see FIG. 4). In this case, the micro-cavity 121 may be provided in the center of the upper portion of the base layer 12.

Then, the second composition 13' is dispensed on the base layer 12 ((c) second dispensing step). In this case, the second composition 13' may be loaded with an active drug.

Optionally, when the second composition 13' is made of powder or liquid, the second composition 13' may be dispensed into the micro-cavity (see FIG. 4). In this case, the second composition 13' may be made of a hydrophilic material or a hydrophobic material.

In this case, the second composition 13' may be dried. Thereby, the core layer 13 formed by the second composition 13' can be prevented from diffusion.

Then, a third composition 14' is dispensed on the base layer 12 to cover the second composition 13' ((d) third dispensing step). In this case, the third composition 14' may be made of a polymer that is not loaded with a drug.

Then, a core layer 13 from the second composition 13' and a shell layer 14 from the third composition 14' are formed by fluidization, centrifugal lithography, or droplet born air blowing (DAB) ((e) forming step). For example, the shell layer 14 may be formed using the centrifugal lithography technique by fluidizing the third composition 14' through a solvent and placing an upper plate on the side opposite to the support 11.

As another example, the shell layer 14 may be formed by the droplet born air blowing method (DAB) in which an upper plate is placed on the side opposite to the support 11 and drying is carried out by wind at low temperature.

Here, when the second composition 13' is hydrophilic, it is affected by the fluidization process, and thus, the core layer 13 may be manufactured in a form similar to that of the shell layer 14.

Accordingly, in the method of manufacturing a multi-layer microneedle structure according to an embodiment of the present invention, the multi-layer microneedle structure 10 can be manufactured according to the manufacturing conditions of the shell layer 14, whereby the multi-layer microneedle structure 10 can be manufactured under the same manufacturing conditions regardless of the type of drug included in the core layer 13. Thus, the microneedle structures for various drugs can be manufactured by the same process.

Further, in the method of manufacturing a multi-layer microneedle structure according to an embodiment of the present invention, since the core layer 13 is not exposed to the outside by the shell layer 14, there is no need to optimize the manufacturing process according to the type of drug, thereby simplifying the manufacturing process and improving manufacturing efficiency.

Furthermore, in the method of manufacturing a multi-layer microneedle structure according to an embodiment of the present invention, by changing the manufacturing conditions for the shell layer 14, the physical properties of the entire multi-layer microneedle structure 10 can be improved, and the drug can be safely protected from the external environment.

Figure 7:
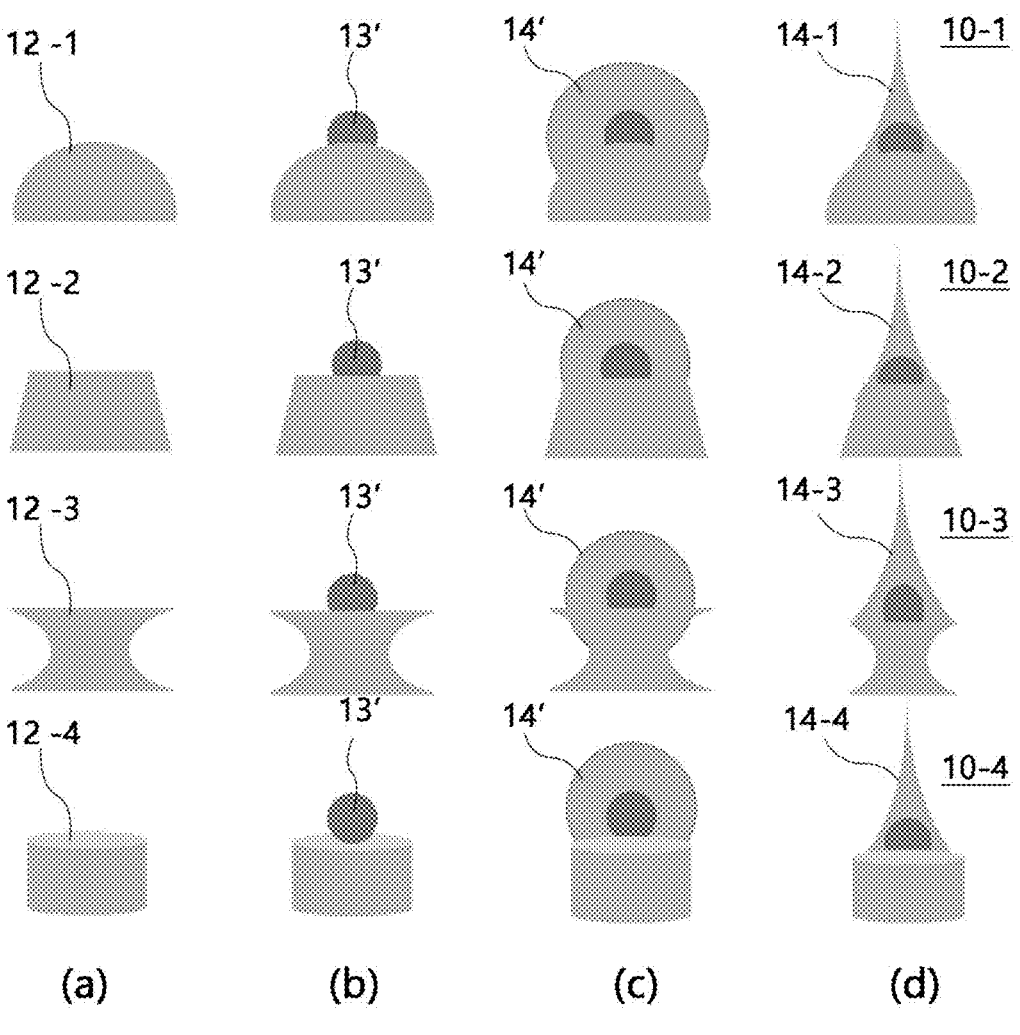
FIG. 7 is a view showing a modified example of a multi-layer microneedle structure according to an embodiment of the present invention.

FIG. 7 is a view showing a modified example of a multi-layer microneedle structure according to an embodiment of the present invention.

Referring to FIG. 7, the manufacturing method of the present invention may manufacture the multi-layer microneedle structures 10-1 to 10-4 in various shapes.

As shown in (a) of FIG. 7, in the first dispensing step and the drying step, a semicircular base layer 12-1, a trapezoidal base layer 12-2, a base layer with a concave middle 12-3, and a cylindrical base layer 12-4 may be manufactured.

As shown in (b) of FIG. 7, the second composition 13' containing the drug is dispensed on each of the base layers 12-1 to 12-4.

As shown in (c) of FIG. 7, the third composition 14' is dispensed on the base layers 12-1 to 12-4 to cover the second composition 13'. In this case, the range of the third composition 14' to be dispensed may vary depending on the shape of the base layers 12-1 to 12-4.

For example, in the case of the semicircular base layer 12-1, the third composition 14' may be formed up to a certain height of the semicircular base layer 12-1. That is, the third composition 14' may be formed from the center of the semicircular base layer 12-1 to both sides at a certain angle. In the case of the trapezoidal base layer 12-2, the third composition 14' may be formed on the entire upper surface of the trapezoidal base layer 12-2. In the case of the base layer having a concave middle 12-3, the third composition 14' may be formed only in a portion except for both sides of the base layer having a middle concave 12-3. In the case of the cylindrical base layer 12-4, the third composition 14' may be formed on the entire upper surface of the cylindrical base layer 12-4.

As shown in (d) of FIG. 7, the shell layers 14-1 to 14-4 are formed by fluidization and centrifugal lithography. In this case, the multi-layer microneedle structures 10-1 to 10-4 may be manufactured to have different overall shapes depending on the shape of the base layers 12-1 to 12-4.

For example, in the case of the semicircular base layer 12-1, the shell layer 14-1 may be formed in a conical shape following the semicircular base layer 12-1. Therefore, the multi-layer microneedle structure 10-1 may be manufactured in a cross-sectional shape having a continuous curve with an outwardly convex lower part and a centrally concave upper part.

In the case of the trapezoidal base layer 12-2, the shell layer 14-2 may be formed in a conical shape extending from the upper surface of the trapezoidal base layer 12-2. Therefore, the multi-layer microneedle structure 10-2 may be formed in a curved cross-sectional shape that forms a straight line up to a certain height and then converges to the center.

In the case of the base layer having a concave middle 12-3, the shell layer 14-3 may be formed in a conical shape on the upper side of the base layer 12-3 having a concave middle. Therefore, the multi-layer microneedle structure 10-3 may be formed in a curved cross-sectional shape that converges to the center following a neck portion having a concave middle.

In the case of the cylindrical base layer 12-4, the shell layer 14-4 may be formed in a conical shape extending from the upper surface of the cylindrical base layer 12-4. Accordingly, the multi-layer microneedle structure 10-4 may be formed in a curved shape converging to the center from a straight lower portion having a certain height.

Figure 8:
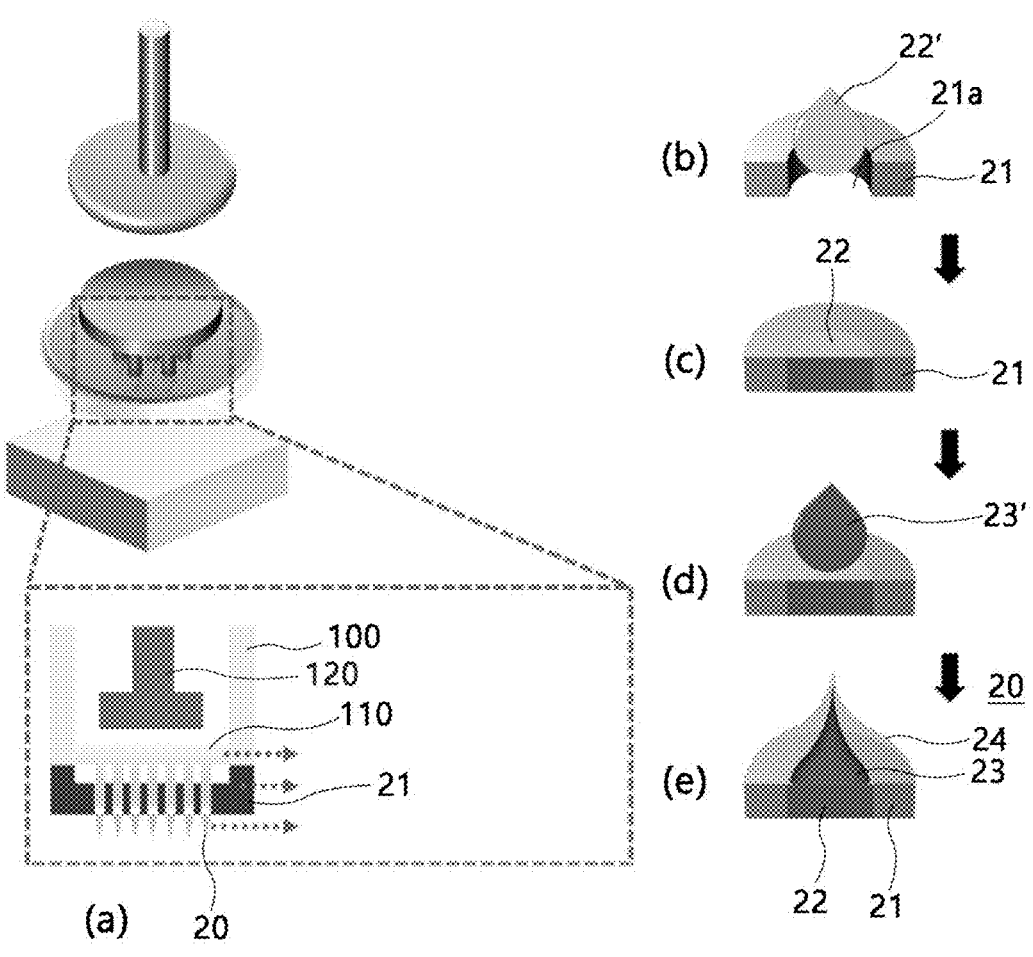
FIG. 8 is a view showing another modified example of a multi-layer microneedle structure according to an embodiment of the present invention.

FIG. 8 is a view showing another modified example of a multi-layer microneedle structure according to an embodiment of the present invention.

As shown in (a) of FIG. 8, the multi-layer microneedle structure 20 may be provided on a perforated plate 21 mounted on an applicator 100. Here, the applicator 100 may include a micro-pillar 110 and a piston 120. As the piston 120 descends, the micro-pillars 110 are inserted into openings 21a of the perforated plate 21 so that the multi-layer microneedle structure 20 can be inserted into a skin 1.

As shown in (b) of FIG. 8, the support is the perforated plate 21 provided with the opening 21a. In the manufacturing method of the multi-layer microneedle structure according to an embodiment of the present invention as described above, the opening 21a may be filled with the first composition 22' in the first dispensing step.

As shown in (c) of FIG. 8, in the drying step, the first composition 22' may form the base layer 22 formed in the opening 21a.

As shown in (d) of FIG. 8, similar to the method for manufacturing the multi-layer microneedle structure according to an embodiment of the present invention as described above, in the second dispensing step, the second composition 23' is dispensed on the base layer 22.

As shown in (d) of FIG. 8, similar to the method for manufacturing the multi-layer microneedle structure according to an embodiment of the present invention as described above, after dispensing the third composition, the multi-layer microneedle structure 20 including the base layer 22, the core layer 23 and the shell layer 24 may be formed on the perforated plate 21 by fluidization and centrifugal lithography.

Figure 9:
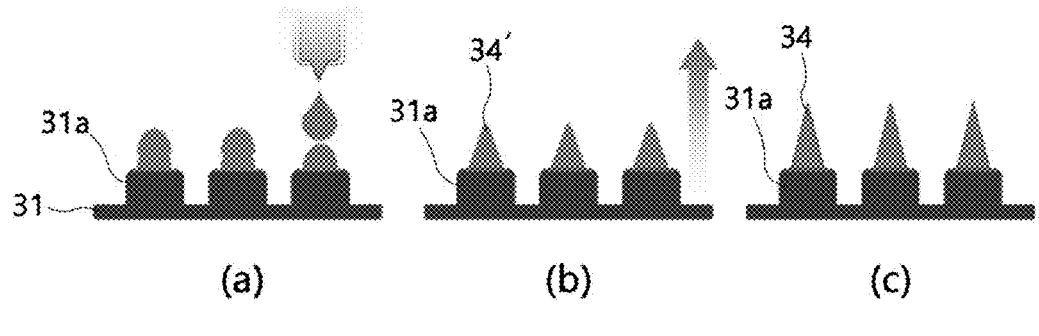
FIG. 9 is a view showing still another modified example of a multi-layer microneedle structure according to an embodiment of the present invention.

FIG. 9 is a view showing still another modified example of a multi-layer microneedle structure according to an embodiment of the present invention.

As shown in (a) of FIG. 9, the multi-layer microneedle structure may be formed on the support 31 provided with the micro-pillars 31a. Similar to the method for manufacturing the multi-layer microneedle structure according to an embodiment of the present invention as described above, the first composition, the second composition and the third composition may be sequentially dispensed on the micro-pillars 31a of the support 31.

As shown in (b) of FIG. 9, the fluidization and centrifugal lithography for the compositions 34' may be performed on the micro-pillars 31a.

As shown in (c) of FIG. 9, the shell layer 34 may be formed on the micro-pillars 31a protruding from the support 31.

Figure 10:
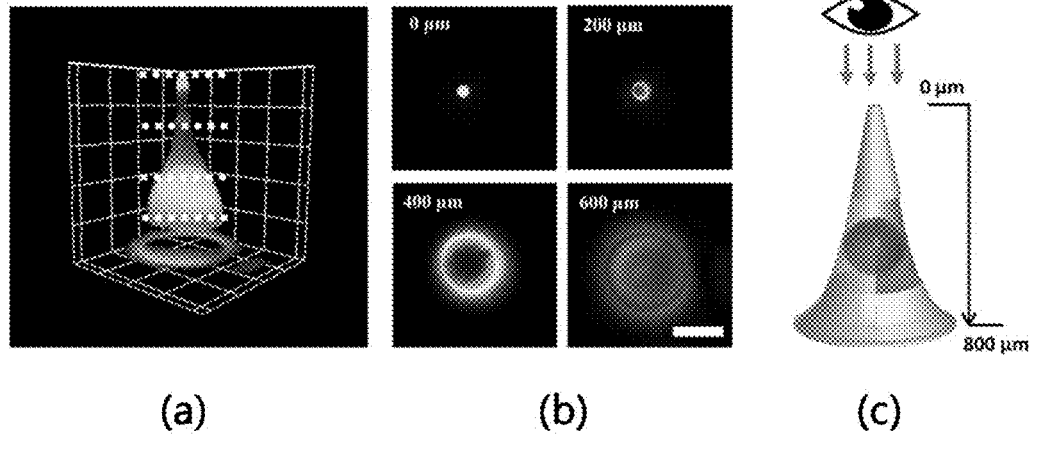
FIG. 10 is a view showing a confocal laser scanning microscopy analysis of a multi-layer microneedle structure according to an embodiment of the present invention.
Figure 11:
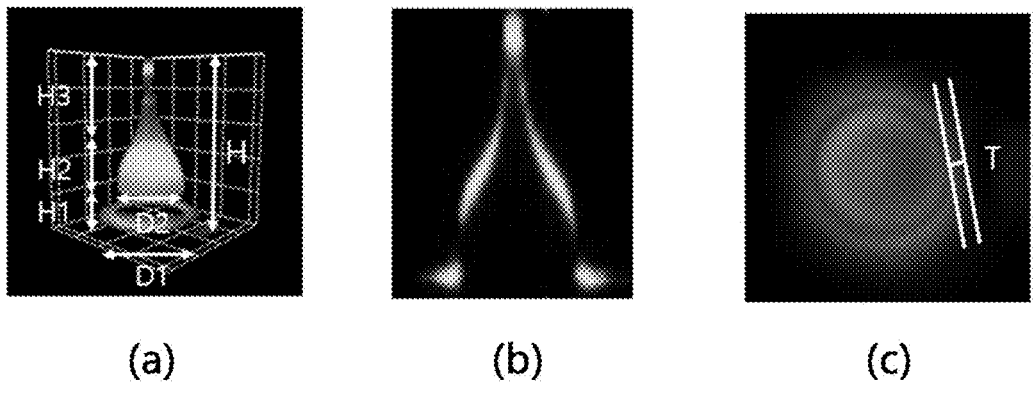
FIG. 11 is a view showing each factor and shell structure of a multi-layer microneedle structure according to an embodiment of the present invention.

FIG. 10 is a view showing a confocal laser scanning microscopy analysis of a multi-layer microneedle structure according to an embodiment of the present invention; and FIG. 11 is a view showing each factor and shell structure of a multi-layer microneedle structure according to an embodiment of the present invention.

Referring to FIG. 10, the multi-layer microneedle structure 10 prepared according to the above-described method was analyzed with a confocal laser scanning microscope.

A cross-sectional image for each height of the multi-layer microneedle structure 10 shown in FIG. 10(a) is shown in FIG. 10(b). In this case, it was based on a distance when the multi-layer microneedle structure was viewed from the top as shown in (c) of FIG. 10. In FIGS. 10 and 11, green indicates the shell layer 14, and red indicates the core layer 13 including the drug. The mixed portion of the shell layer 14 and the core layer 13 containing the drug is indicated by yellow.

The upper end (0 μm to 200 μm) of the multi-layer microneedle structure 10 do not contain the drug, and the lower end (400 μm to 600 μm) include the drug. From the cross-sectional image of 600 μm, it can be confirmed that the core layer 13 is completely surrounded by the shell layer 14.

As shown in (a) of FIG. 11, a factor for each part of the multi-layer microneedle structure 10 is defined. Here, H is the total height of the base layer 12, the core layer 13 and the shell layer 14; H1 is the height of the base layer 12; H2 is the height of the core layer 13; and H3 is the height from the tip of the core layer 13 to the tip of the shell layer 14. Further, D1 is the diameter of the base layer 12, and D2 is the diameter of the lower surface of the core layer 13.

As shown in (b) of FIG. 11, the shell layer 14 forms the outer shape of the multi-layer microneedle structure 10. In this case, the shell layer 14 surrounds the core layer 13 and thus has an internal space corresponding to the core layer 13.

As shown in (c) of FIG. 11, T is the thickness of the shell layer 14 outside the core layer 13. That is, T is the thickness of the shell layer 14 surrounding the core layer 13 in a horizontal cross-section.

Figure 12:
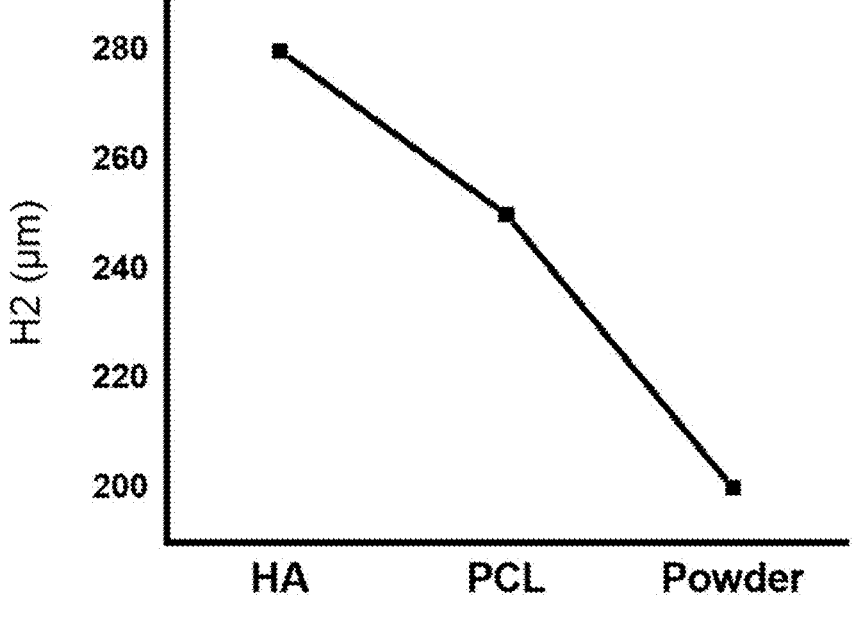
FIG. 12 is a graph illustrating a formation height according to a material of a core layer in a multi-layer microneedle structure according to an embodiment of the present invention.
Figure 13:
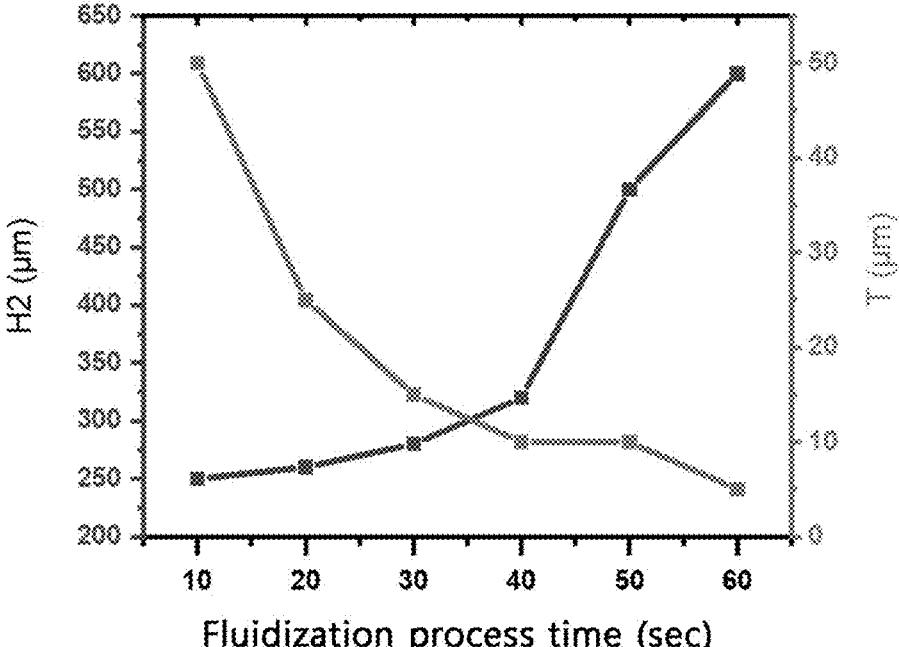
FIG. 13 is a graph showing a height of a core layer and a thickness of a shell layer outside the core layer according to a fluidization process time in a multi-layer microneedle structure according to an embodiment of the present invention.

FIG. 12 is a graph illustrating a formation height according to a material of a core layer in a multi-layer microneedle structure according to an embodiment of the present invention; and FIG. 13 is a graph showing a height of a core layer and a thickness of a shell layer outside the core layer according to a fluidization process time in a multi-layer microneedle structure according to an embodiment of the present invention.

In order to identify the effect of manufacturing process conditions on the multi-layer microneedle structure 10, the following experiment was performed.

First, in order to identify the change in the shape of the core layer 13 according to the manufacturing process, a multi-layer microneedle structure 10 having different core layers 13 was prepared. Here, hyaluronic acid (HA), PCL and powder were used for the core layer (13).

As shown in FIG. 12, in the case of hyaluronic acid (HA), which is hydrophilic, the height of the core layer 13 is changed by the manufacturing process (particularly, fluidization process) of the multi-layer microneedle structure 10. This varies depending on the fluidization process time, but when the fluidization process time is fixed to 30 seconds, the height of the core layer 13 was 280 μm.

In the case of PCL, since it is hydrophobic, there was little change in the core height due to the manufacturing process (particularly, fluidization process) of the multi-layer microneedle structure 10. When the fluidization process time is fixed to 30 seconds, the height of the core layer 13 was 250 μm.

In the case of powder, there was little change in the core height due to the manufacturing process (particularly, fluidization process) of the multi-layer microneedle structure 10. In this case, it is determined by the height of the micro-cavity of the base layer 12. The height of the core layer 13 was 200 μm.

As can be seen from the above, the multi-layer microneedle structure 10 is affected by the manufacturing process according to the composition of the core layer 13. In particular, when the core layer 13 is hydrophilic, the manufacturing process may affect the shape of the core layer 13.

Next, a change in the shape of the hydrophilic core layer 13, which is greatly affected by the fluidization process, was tested. In this case, hyaluronic acid (HA) was used for the core layer 13. The multi-layer microneedle structure 10 was manufactured while fixing the overall height H of the multi-layer microneedle structure 10, the height H1 of the base layer 12 and the diameter D1 of the base layer 12 and increasing the fluidization process time from 10 seconds to 60 seconds.

Here, the overall height H of the multi-layer microneedle structure 10 was 800 μm, the height H1 of the base layer 12 was 200 μm, and the diameter D1 of the base layer 12 was 400 μm.

As shown in FIG. 13, the height H2 of the core layer 13 was found to be proportional to the fluidization process time. On the other hand, the thickness T of the shell layer 14 outside the core layer 13 was found to be inversely proportional to the fluidization process time.

That is, as the fluidization process time increases, the height H2 of the core layer 13 gradually increases because the core layer 13 is changed similarly to the shell layer 14. In addition, when the fluidization process time is increased, the thickness T of the shell layer 14 outside the core layer 13 is gradually decreased because the shell layer 14 is changed in the height direction. Accordingly, the height H2 of the core layer 13 is inversely proportional to the thickness T of the shell layer 14 outside the core layer 13.

In this case, it can be seen that the height H3 from the tip of the core layer 13 to the tip of the shell layer 14 is affected by the height H2 of the core layer 13, because the overall height H of the multi-layer microneedle structure 10 and the height H1 of the base layer 12 are fixed.

That is, the height H3 from the tip of the core layer 13 to the tip of the shell layer 14 is a value obtained by subtracting the height H1 of the base layer 12 and the height H2 of the core layer 13 from the overall height H of the multi-layer microneedle structure 10. Accordingly, the height H3 from the tip of the core layer 13 to the tip of the shell layer 14 decreases as the height H2 of the core layer 13 increases. That is, the height H3 from the tip of the core layer 13 to the tip of the shell layer 14 is inversely proportional to the height H2 of the core layer 13. As a result, the height H3 from the tip of the core layer 13 to the tip of the shell layer 14 is inversely proportional to the fluidization process time.

In addition, the height H3 from the tip of the core layer 13 to the tip of the shell layer 14 is proportional to the thickness T of the shell layer 14.

Although an embodiment of the present invention have been described above, the spirit of the present invention is not limited to the embodiment presented in the subject specification; and those skilled in the art who understands the spirit of the present invention will be able to easily suggest other embodiments through addition, changes, elimination, and the like of elements without departing from the scope of the same spirit, and such other embodiments will also fall within the scope of the present invention.

The invention claimed is:

1. A multi-layer microneedle structure comprising:
a base layer formed on a support;
a core layer formed on the base layer and containing a drug; and
a shell layer formed on the base layer to cover the core layer,
wherein the relationship between the thickness T of the shell layer outside the core layer and the height H2 of the core layer is determined according to the material constituting the core layer,
wherein the shell layer covers the core layer such that the core layer is not exposed to the outside.

2. The multi-layer microneedle structure according to claim 1, wherein the core layer is made of a hydrophilic material, and
the height H2 of the core layer is inversely proportional to the thickness T of the shell layer outside the core layer.

3. The multi-layer microneedle structure according to claim 1, wherein the core layer is made of a hydrophobic material, and
the height H2 of the core layer is constant regardless of the thickness T of the shell layer outside the core layer.

4. The multi-layer microneedle structure according to claim 1, wherein the thickness T of the shell layer outside the core layer is inversely proportional to the fluidization process time for forming the core layer and the shell layer.

5. The multi-layer microneedle structure according to claim 1, wherein the thickness T of the shell layer outside the core layer is the smallest at a bonding surface between the core layer and the base layer.

6. The multi-layer microneedle structure according to claim 1, wherein the thickness T of the shell layer outside the core layer is uniform throughout the core layer.

7. The multi-layer microneedle structure according to claim 2, wherein when the total height H of the base layer, the core layer and the shell layer, and the height H1 of the base layer are constant, the height H2 of the core layer is inversely proportional to the height H3 from the tip of the core layer to the tip of the shell layer.

8. The multi-layer microneedle structure according to claim 1, wherein the base layer has a micro-cavity on an upper side thereof, and the core layer is made of powder or liquid and is provided in the micro-cavity.

9. The multi-layer microneedle structure according to claim 8, wherein the height H2 of the core layer is determined by the height of the micro-cavity.

10. The multi-layer microneedle structure according to claim 1, wherein the base layer is formed on micro-pillars formed on the support.

11. The multi-layer microneedle structure according to claim 1, wherein the support is a perforated plate having an opening, and the base layer is formed by filling the opening.

12. A method of manufacturing a multi-layer microneedle structure, the method including:

a first dispensing step of dispensing a first composition on a support;

a drying step of drying the first composition to form a base layer;

a second dispensing step of dispensing a second composition comprising a drug on the base layer;

a third dispensing step of dispensing a third composition on the base layer to cover the second composition; and a forming step of forming a core layer from the second composition and a shell layer from the third composition by fluidization and centrifugal lithography techniques,

wherein the shell layer covers the core layer such that the core layer is not exposed to the outside.

13. The method of manufacturing a multi-layer microneedle structure according to claim 12, wherein the second composition is made of a hydrophilic material, and the height H2 of the core layer is proportional to the fluidization process time.

14. The method of manufacturing a multi-layer microneedle structure according to claim 12, wherein the second composition is made of a hydrophobic material, and the height H2 of the core layer is constant regardless of the fluidization process time.

15. The method of manufacturing a multi-layer microneedle structure according to claim 12, wherein the thickness T of the shell layer outside the core layer and the height H3 from the tip of the core layer to the tip of the shell layer is inversely proportional to the fluidization process time.

16. The method of manufacturing a multi-layer microneedle structure according to claim 12, wherein the drying step further comprises forming a micro-cavity on the base layer, and the second composition is made of powder or liquid, wherein in the second dispensing step, the second composition is dispensed in the micro-cavity.

17. The method of manufacturing a multi-layer microneedle structure according to claim 12, wherein the support includes micro-pillars, and in the first dispensing step, the first composition is dispensed on the micro-pillars.

18. The method of manufacturing a multi-layer microneedle structure according to claim 12, wherein the support is a perforated plate having an opening, and in the first dispensing step, the first composition is filled in the opening.

19. The method of manufacturing a multi-layer microneedle structure according to claim 12, wherein the second dispensing step further includes drying the second composition.

* * * * *